(12) United States Patent
Imran

(10) Patent No.: US 10,307,551 B2
(45) Date of Patent: *Jun. 4, 2019

(54) CONTROLLED INHALER FOR DISTRIBUTING INHALANT ACCORDING TO INHALATION VELOCITY

(71) Applicant: InCube Labs, LLC, San Jose, CA (US)

(72) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 121 days.

This patent is subject to a terminal disclaimer.

(21) Appl. No.: 15/263,768

(22) Filed: Sep. 13, 2016

(65) Prior Publication Data

US 2017/0065778 A1 Mar. 9, 2017

Related U.S. Application Data

(63) Continuation of application No. 14/225,151, filed on Mar. 25, 2014, now Pat. No. 9,463,291, which is a
(Continued)

(51) Int. Cl.
*A61M 15/00* (2006.01)
*A61M 11/00* (2006.01)
*A61M 16/00* (2006.01)

(52) U.S. Cl.
CPC ...... *A61M 15/0091* (2013.01); *A61M 11/007* (2014.02); *A61M 15/0095* (2014.02);
(Continued)

(58) Field of Classification Search
CPC .......... A61M 15/0093; A61M 15/0091; A61M 15/0095; A61M 16/0003;
(Continued)

(56) References Cited

U.S. PATENT DOCUMENTS 7,147,170 B2 12/2006 Nguyen et al.
7,832,394 B2 * 11/2010 Schechter ........... A61M 15/009
128/200.11
(Continued)

OTHER PUBLICATIONS

International Preliminary Report on Patentability dated Apr. 7, 2011 in PCT/US2009/058661.
(Continued)

*Primary Examiner* — Steven O Douglas
(74) *Attorney, Agent, or Firm* — Mahamedi IP Law LLP; Joel Harris

(57) ABSTRACT

An inhaler is provided that includes a controller, a driver, an atomizer and one or more sensors for detecting information about a velocity of inhalation of a user of the inhaler. The controller is configured to dispense an inhalant from the inhaler during an inhalation of the user based on information about the velocity of inhalation of the user. Such information can include a duration of maximum inhalation velocity or an increase or maximum in the acceleration in inhalation velocity. Embodiments of the inhaler can be used to enhance the delivery of drugs and therapeutic agents for those patients having a weakened respiratory system who are unable to take a deep or full breadth, e.g., patients having asthma or COPD. Embodiments of the inhaler can be used to deliver a variety of drugs and therapeutic agents including agents for the treatment of asthma, diabetes, epilepsy and heart disease.

16 Claims, 3 Drawing Sheets

Related U.S. Application Data continuation of application No. 12/568,617, filed on Sep. 28, 2009, now Pat. No. 8,695,587.

(60) Provisional application No. 61/100,265, filed on Sep. 26, 2008.

(52) U.S. Cl.
CPC ............... *A61M 2016/0018* (2013.01); *A61M 2016/0021* (2013.01); *A61M 2016/0039* (2013.01); *A61M 2205/276* (2013.01); *A61M 2205/6009* (2013.01); *A61M 2205/6018* (2013.01); *A61M 2205/6027* (2013.01); *A61M 2230/40* (2013.01)

(58) Field of Classification Search
CPC .. A61M 2016/0018; A61M 2016/0021; A61M 2016/0039; A61M 2205/276; A61M 11/007; A61M 2205/6009; A61M 2205/6018; A61M 2205/6027; A61M 2230/40
USPC ............ 128/200.14, 200.22, 203.12, 204.23, 128/204.26, 200.21
See application file for complete search history.

(56) References Cited

U.S. PATENT DOCUMENTS

| 8,082,917 | B2 | 12/2011 | Ooida |
| 2002/0073991 | A1 | 6/2002 | Gonda |
| 2004/0123864 | A1 | 7/2004 | Hickey et al. |
| 2004/0231667 | A1 | 11/2004 | Horton et al. |
| 2005/0183725 | A1 | 8/2005 | Gumaste et al. |
| 2005/0274377 | A1* | 12/2005 | Gonda .............. A61M 15/0045 128/200.14 |
| 2007/0044793 | A1 | 3/2007 | Kleinstreuer et al. |
| 2007/0125370 | A1 | 6/2007 | Denyer et al. |
| 2007/0240712 | A1 | 10/2007 | Fleming et al. |
| 2008/0011292 | A1 | 1/2008 | Sugita et al. |

OTHER PUBLICATIONS

International Search Report and Written Opinion and Notice re: same dated Apr. 30, 2010 for International Application No. PCT/US2009/058661.

* cited by examiner

CONTROLLED INHALER FOR DISTRIBUTING INHALANT ACCORDING TO INHALATION VELOCITY

RELATED APPLICATIONS

This application is a continuation of U.S. patent application Ser. No. 14/255,151, filed Mar. 25, 2014, which is a continuation of U.S. patent application Ser. No. 12/568,617, filed Sep. 28, 2009, now U.S. Pat. No. 8,695,587, issued Apr. 15, 2014, which claims the benefit of priority to Provisional U.S. Patent Application No. 61/100,265, filed Sep. 26, 2008; the aforementioned priority applications are hereby incorporated by reference in their entirety for all purposes.

FIELD OF THE INVENTION

Embodiments described herein relate to an inhaler for delivering an inhalant to a patient. More specifically, embodiments described herein relate to a controlled inhaler for distributing inhalant according to inhalation velocity or other inhalation characteristic.

BACKGROUND

Inhalers are common devices for delivering various medications (including drugs and other therapeutic agents) to a patient (also referred to herein as a user) in an inhaled aerosol form referred to herein as inhalant. Many medical conditions and diseases may be treated with inhalers including respiratory conditions such as asthma and chronic obstructive pulmonary disease (COPD) as well as non pulmonary conditions including diabetes. COPD which includes emphysema and chronic bronchitis is a particularly debilitating disease affecting as many as 24 million Americans and killing more than 100,000 each year. It involves thickened and narrowed lung airways and excess mucous. Symptoms include persistent coughing and severe shortness of breath.

Inhalers provide a benefit of ensuring any drug or other therapeutic agent distributed as an inhalant is quickly delivered to a target pulmonary site (e.g., the bronchial tubes in the case of asthma) or absorbed into the bloodstream, as the human respiratory system is well adapted to absorb aerosol or other inhalants into the blood stream. In fact, many large-molecule drug compounds including proteins and peptides are easily absorbed by the lungs, and once absorbed in the deep lung, they pass readily into the bloodstream (through a single-cell layer known as the pulmonary epithelium) without the need for enhancers that are required by other noninvasive routes.

However many patients who use inhalers have compromised respiratory function such that they are not able to take a deep or forceful enough breath for the inhalant to reach the bronchial tubes, let alone the deep lung or other target site in sufficient quantities to treat the particular condition (either in terms of the drug having the desired affect at the site or being absorbed in sufficient quantities into the blood stream to have the desired effect on another target site). This is particularly the case for COPD where patients have severe shortness of breath and frequent bouts of coughing. Even for non respiratory-compromised patients, variations in breathing technique can result in significant variation in the amount of drug delivered to the target site including deep into the lung resulting in possible inconsistent dosing from breath to breath. Thus, there is need for an improved inhaler.

DETAILED DESCRIPTION OF THE INVENTION

Embodiments provide for a mechanism for controlled delivery of drugs and other therapeutic agents to a user (e.g. patient) in an inhaled form. More specifically, embodiments include a mechanism that obtains information from a user's inhalation and/or other aspect of user's respiration process in order to control the delivery of the drug or other therapeutic agent. In this way, an inhalant carrying a drug or therapeutic agent is delivered to a user in a manner that is specific to characteristics about the user's inhalation or respiratory process.

According to an embodiment, an inhaler is provided that is capable of controlling the release and delivery of inhalant to a user based on an inhalation velocity of the user. Typically, the inhalant comprises an aerosol form of a drug. It can be either in liquid or solid form and may include one or more pharmaceutical excipients known in the art (e.g., binders).

Embodiments recognize that some individuals suffer from medical conditions such as asthma, acute bronchitis, COPD (chronic obstructive pulmonary disease) and like conditions that weaken the respiratory system. Such individuals may be at a disadvantage in using inhalers, in that their weakened respiratory system hinders or impedes the inhalant from sufficiently penetrating or diffusing into the respiratory system to achieve the desired or full effect of the drug. Many conventional approaches have relied on manually operated compression mechanisms to force inhalant into the user. Such conventional approaches may be difficult to operate, at least to achieve optimal results. In contrast to conventional approaches, one or more embodiments provide a controlled inhaler that automatically triggers the release and dispensing of the inhalant at an appropriate instance after inhalation is initiated by a user. The appropriate instance may be determined by analyzing the velocity of the user's inhalation or other characteristic. In one embodiment, a velocity profile is estimated for the user and applied to determine when, during the time course of inhalation, the inhalant is to be released for a given user.

Figure 1:
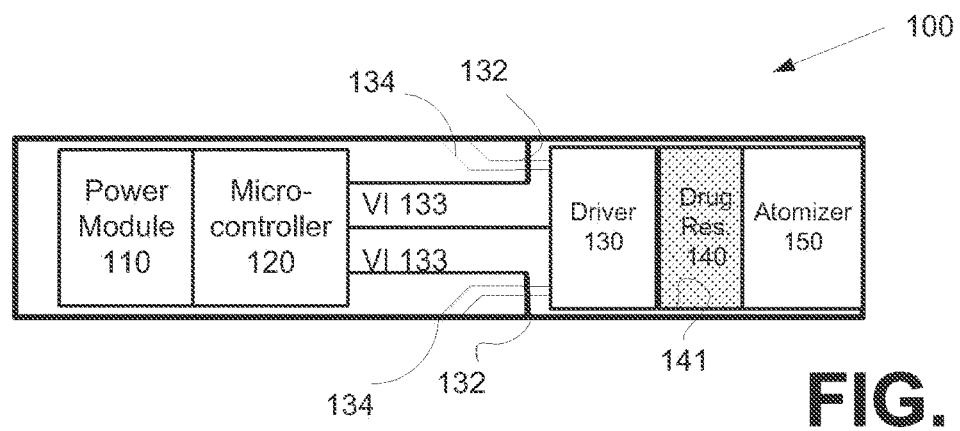
FIG. 1 is a schematic view of an embodiment of a controlled inhaler.
Figure 2:
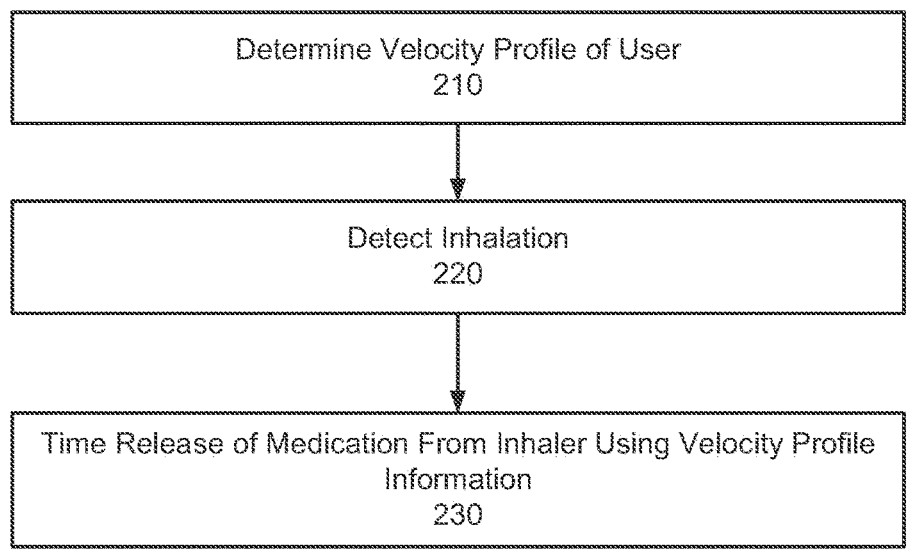
FIG. 2 is a flow chart illustrating an embodiment of a method of the for using the inhaler.
Figure 3:
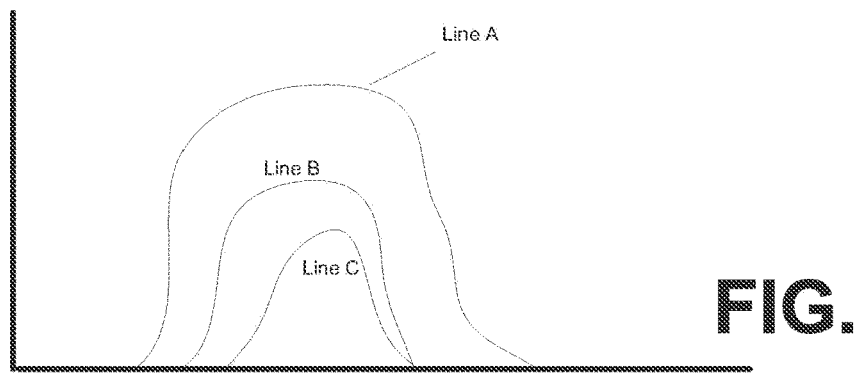
FIG. 3 is a time graph illustrating time profiles for various events used or generated by embodiments described herein.

FIG. 1 illustrates an inhaler, according to one or more embodiments. According to an embodiment, an inhaler 100 includes a power module 110, a controller 120 (e.g. microcontroller), a driver 130, a drug reservoir 140 and an atomizer 150.

The power module 110 may correspond to a battery unit that powers that controller 120. Suitable batteries include alkaline, lithium ion and like chemistries known in the portable electronic device arts. The controller 120 controls the driver 130 in dispensing inhalant from the reservoir 140 through the atomizer 150. The driver 130 drives inhalant 141 in liquid or particle form through the atomizer 150. Driver 130 can comprise a mechanical pump such as a spring loaded piston pump which can be manual or powered. It can also comprise a source of compressed inert gas (e.g., helium, air etc,) that provides the pressure for driving the inhalant through the atomizer 150. Driver 130 can also be controlled by the patient's inhalation velocity profile (or other information about the patient's inhalation velocity or inhalation characteristic) or by real time measurement of inhalation velocity so as to modulate the driving pressure over the course of the patient's inhalation. For example, driver 130 can be configured to generate higher driving pressure and thus a faster ejected velocity of the inhalant during the slower portions of the patient's inhalation (i.e. those portions having decreased velocity). In this way, a substantially uniform or more uniform delivery of inhalant (e.g., dose unit delivered/per unit time) can be achieved over the course of an inhalation. This in turn, improves the amount of inhalant delivered during an inhalation and thus the amount ultimately absorbed into the patient's blood stream through the alveoli and small blood vessels in the lung.

The inhaler 100 includes inlets 134 that correspond to conduits from which the user draws in air when using the inhaler 100. Inlets 134 can have various sizes and shapes which can be selected depending one or more of the patient's condition (e.g. asthmatic), respiratory capacity (e.g., reduced tidal volume, shortness of breath, etc), the patient's age (e.g., adult vs. child), and the drug to be administered (e.g., large molecule vs. small molecule). In particular embodiments, inlets 134 can be controllable by controller 110 so that they can be open or closed in response to one or more factors (e.g., the patient's velocity profile, respiratory capacity, etc). Movement of inlets 134 can even be done dynamically over the course of the patient's inhalation so as to account for variations in the inhalation e.g., due to coughing, wheezing, etc. Opening and closing of inlets 134 can be achieved through a variety of means including, for example, solenoid valves, reed valves, piezo-electric valves and similar devices. In various embodiments, one or more of these devices can itself comprise an inlet 134 or can be coupled to the inlet.

In an embodiment, sensors 132 are positioned with or near the inlets to measure velocity or other motion characteristics of the airflow through the inlets when the user inhales. In one embodiment, sensors 132 measure inflow velocity and provide inhalation velocity information 133 to the controller 110. The controller 110 is configured to use the information 133 to develop an estimation of the inhalation velocity profile of the user. In this way, the controller 110 is able to make a determination or predictive determination of instance of release, or alternatively of force/velocity required (or likely required) at a particular instance in the inhalation of a given user. Sensors 133 can comprise various air velocity sensors known in the art including optical, acoustical or anemometry-based sensors or combinations thereof. Sensors 133 can also be configured to detect the direction of air flow so as to be able to sense when the patient is coughing. This information can then be used to stop the release of inhalant during this duration so that inhalant is not wasted. Further, controller 110 can be configured to increase the amount of dispensed aerosoled drug during the remainder of inhalation so that the desired delivered dose is not decreased due to, for example, coughing or wheezing.

Reservoir 140 contains a supply of inhalant 141 in its non-aerosoled form; the supply can be in solid or liquid form. The inhalant can contain the drug only but also may contain one or more excipients. In various embodiments, reservoir 140 can be fixed to the inhaler or can be detachable by the user. In the later case, the reservoir 140 can comprise a detachable cartridge configured to snap or twist onto inhaler 100. Also for detachable embodiments, the user can obtain the reservoir at his or her pharmacy. The amount of inhalant in the reservoir can be pre-packed at the factory or can be prepared and added by the pharmacist depending upon the prescription. In particular embodiments, the reservoir can also have multiple chambers including chambers for solid inhalant and a second chamber for a liquid that is mixed with the solid inhalant to generate a spray in the atomization chamber 150 as is described herein. It can also contain chambers for a first and second inhalant which can comprise different drugs or the same drug having different formulations, e.g., one formulation to produce a first aerosoled particle size and a second formulation to produce a second particle size. Such embodiments can allow for the delivery of different sized particles during different portions of an inhalation so as to optimize or otherwise enhance the delivery of drug during inhalation. For example, smaller sized particles can be generated during portions of inhalation having a reduced inhalation velocity and versa visa.

For both detachable and non detachable embodiments, reservoir 140 can also include various electronic identification means such as an electronic ID chip that communicates with controller 120. The ID chip (not shown) can include various information about the particular inhalant such as the particular drug contained within the inhalant, the dose to be administered, the total number of doses that can be administered, number of allowable doses in a particular duration (e.g., for opiates or other pain medication), the optimal velocity profile for releasing and dispensing the inhalant and the shelf life/expiration date of the inhalant. The ID chip can also include a unique identifier associated with the user's inhaler such that the microprocessor 120 will only accept a reservoir that has the unique identifier, otherwise it will not dispense inhalant. In this way, mistaken or illegal use of a particular inhalant can be prevented. The ID chip can also include various respiratory and/or medical profile data unique to the patient such as information on their particular disease and/or disease stage as well as various respiratory and inhalation characteristics including an inhalation velocity profile, tidal volume etc. It may also include parametric data for the population or subpopulation of patients to which the user belongs (e.g., dose requirements and respiratory velocity profiles for pediatric asthmatics vs. asthmatics over 65). This information can be correlated to data collected by the inhaler and used to fine tune or otherwise optimize the delivery of inhalant to the desired target site of a particular user.

Atomizer 150 serves to atomize or aerosolize inhalant compound from reservoir 140. In various embodiments, atomizer 150 can comprise a chamber containing inlets and outlets (or other openings) and a vibrational member, such as a piezoelectric membrane or layer, which is actuated by an electrical current. As inhalant (in solid or liquid form) is driven through the atomizer, the vibrational member is triggered, causing the inhalant to be aerosolized. Pressure from the driver may force the aerosolized inhalant through the outlet, and the user can inhale the aerosolized spray to supply the inhalant to the patient's bronchial tubes, lungs or other target pulmonary site.

In various embodiments, atomizer 150 (also known as aerosolization device 150) can be configured to aerosolize solid or liquid forms of inhalant. In particular embodiments, it can also be configured to convert a solid inhalant into a liquid spray by mixing in a liquid into the atomizing chamber during the aerosolizing process. The aerosolization process can also be controlled based upon the patient's inhalation velocity profile or other inhalation characteristic of the respiratory cycle. For example, the vibration frequency of the vibrational member can be modulated over the course of the patient's inhalation velocity profile. Higher frequencies can be used during periods of slower inhalation velocity and vice-versa. The frequency can also be adjusted based on the particle size and/or particle mass of the inhalant. Higher frequencies can be used for larger particle sizes and/or mass and vice versa.

In an embodiment, the controller 120 is configured to (i) detect inhalation use of the inhaler 100, (ii) provide an automatic response to the inhalation action by delaying release of the inhalant until an instance in which the inhalation velocity is estimated, deemed or otherwise predicted to be optimal or prime for deep penetration into the user's respiratory system. When the user has a weak respiratory system, for example, adequate penetration into the respiratory system may be best when the release of inhalant occurs when the user's inhalation velocity has significantly increased after an inhalation has started. Accordingly, in one embodiment, the instance of deployment is determined from inhalant velocity profile information of the user. The inhalant velocity profile information may be determined through use of velocity sensors 132 that are positioned within or near the inlets 134. The inhalant velocity information may be either pre-determined, or alternatively, estimated on the fly or on a real time basis by the controller through input from the velocity sensors 132. The controller's response may be in the form of triggering the driver 130 to drive the non-aerosoled inhalant from reservoir 140 through the atomizer 150 while inhalation is taking place as well as modulating the driving the driving pressure generated by the driver to drive the non-aerosoled inhalant through the atomizer.

FIG. 2 illustrates a methodology or algorithm that may be implemented by the controller 110 when the inhaler 100 is in use, according to an embodiment. It should be appreciated that the order of these steps in this methodology is exemplary and other orders are contemplated. Step 210 provides that the user's inhalation velocity profile is determined. In one embodiment, the inhalation velocity profile is determined through a training process, where the user takes sample breaths before using the inhaler to receive a dose of the inhalant. The controller 120 may determine the information 133 from the user's sample breaths. The controller 110 then develops a velocity profile of the user's inhalation.

As an alternative or addition, the velocity information may be determined on-the-fly or real time basis. For example, controller 110 may gauge when to trigger release and dispensing of the inhalant based on when maximum acceleration in the inflow of the inhalation occurs. The assumption may be that maximum acceleration occurs before maximum velocity. Such a period and/or point of maximum acceleration may occur as an inflection point in the inhalation velocity profile. As still another alternative, the release and dispensing of inhalant may simply be timed to occur at some instance after the user starts breathing. In still other embodiments, various other inhalation characteristics can be employed to control the release and dispensing of inhalant.

Step 220 is performed when the inhalation device 100 is in use. In step 220, inhalation use of the device is detected. This may correspond to the user inhaling through the device.

Step 230 provides that the controller 110 activates the driver 130 to time the release of the medication to coincide with a moment that is deemed to be optimal for dispensing of the medication. The velocity profile of the user's inhalation, as determined in step 210, is used to determine the instance when the controller 110 activates the driver 130 and/or causes release and dispensing of the inhalant. This instance corresponds to some duration after inhalation is initiated, based on, for example, predictive determinations of the controller 110.

FIG. 3 is a time graph illustrating embodiments described herein. In FIG. 3, the user inhales as shown by line A. A breath may last, for example, between 2-6 seconds. Line B shows the timing of the inhalant release through inhaler 100. Line C shows an estimation of how the inhalant reaches its potential maximum penetration in the respiratory system. As shown, dispensing of the inhalant may be initiated at some instance just prior to when the maximum velocity is believed to occur. As shown, the inhalant achieves full penetration into the user's respiratory system at some point after dispensing has begun.

An illustrative embodiment of a method of using inhaler 100 will now be described. The inhaler has two modes of operation, a training mode and a drug/inhalant dispensing mode. During the training mode, the patient takes one or more breaths holding the device in their mouth. Air enters through the intakes and the velocity sensors sense the velocity of their breath over time and a velocity time profile is generated. Several breaths may be required to generate the profile. When the profile is generated, the inhaler can configured to beep or otherwise signals the user that it is ready for the dispensing of inhalant.

During the drug dispensing mode, the patient takes a series of breaths holding a portion of the inhaler in their mouth, during each breath, the controller synchronizes the release and dispensing of inhalant with a peak velocity portion of the patient's breath. It does this by comparing the instant inhalation velocity to the velocity profile (e.g., that generated during the training mode and/or generated real time). Depending upon the velocity profile and other factors (e.g. particle size, particle weight etc), the device determines how many breaths are needed to dispense a desired amount of a particular drug/inhalant. As the patient inhales during the dispensing mode, the device also senses the number and velocity profile of each breath and when the required number of breaths has been taken, the device signals the patient when dispensing is complete. Alternatively, the device can keep beeping until the desired number amount of drug/inhalant has been dispensed. In this way, the dispensing of an aerosolized drug is optimized because it occurs during the period of maximum air flow/velocity into the patient's lungs allowing the drug to go into the deeper portions of the lung providing a much greater surface area for absorption of the drug. Also, drug/inhalant is also not dispensed during other portions of the breath allowing for a drug wash out period. The period of drug/inhalant dispensing during the patient's breath can be determined by velocity as well as the characteristics of the particular drug/inhalant, such as particle size and how readily it is absorbed through lung tissue into the blood stream.

Embodiments of inhaler 100 and various methods of use can be adapted for dispensing a variety of inhaled drugs to treat a number of conditions. For example, in many embodiments, inhaler 100 can be adapted for delivering inhaled medication to the bronchial tubes for treatment of asthma and COPD. In other embodiments, inhaler 100 can be adapted for delivering inhaled medication into the deep lung tissue for absorption into the blood stream. Particular embodiments can be adapted to deliver inhaled insulin into the deep lung tissue for absorption into the blood stream for treatment of diabetes and related diseases. The insulin can comprise a mammalian, human or synthetically derived/modified form of insulin as known in the art.

Figure 4A:
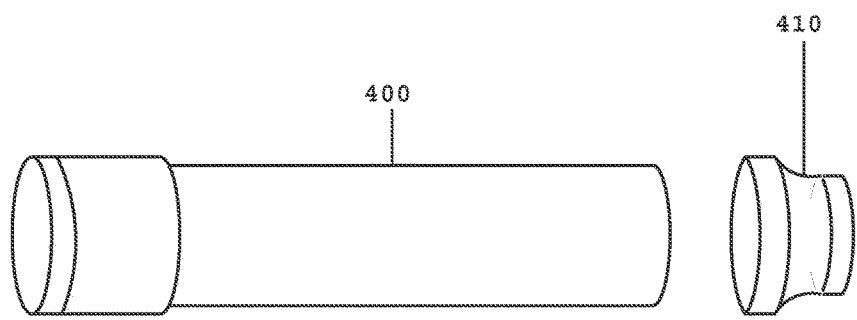
FIG. 4A and FIG. 4B perspective views illustrating an embodiment of the inhaler having a detachable section.
Figure 4B:

FIG. 4A and FIG. 4B illustrate a variation or alternative to embodiments such as described above. In particular, FIG. 4A illustrates an implementation in which a section 410 of an inhaler 400 is detachable and replaceable. As described above, for example, a user may replace cartridges that contain a prescribed drug. The replaceable section 410 may include a drug reservoir 140 (e.g., such as that shown in FIG. 1). As an alternative or addition, the removable section 410 may include the atomizer 150 (e.g., such as that shown in FIG. 1) and/or the driver 130 (FIG. 1), as well as optionally other elements of the device.

Figure 5:
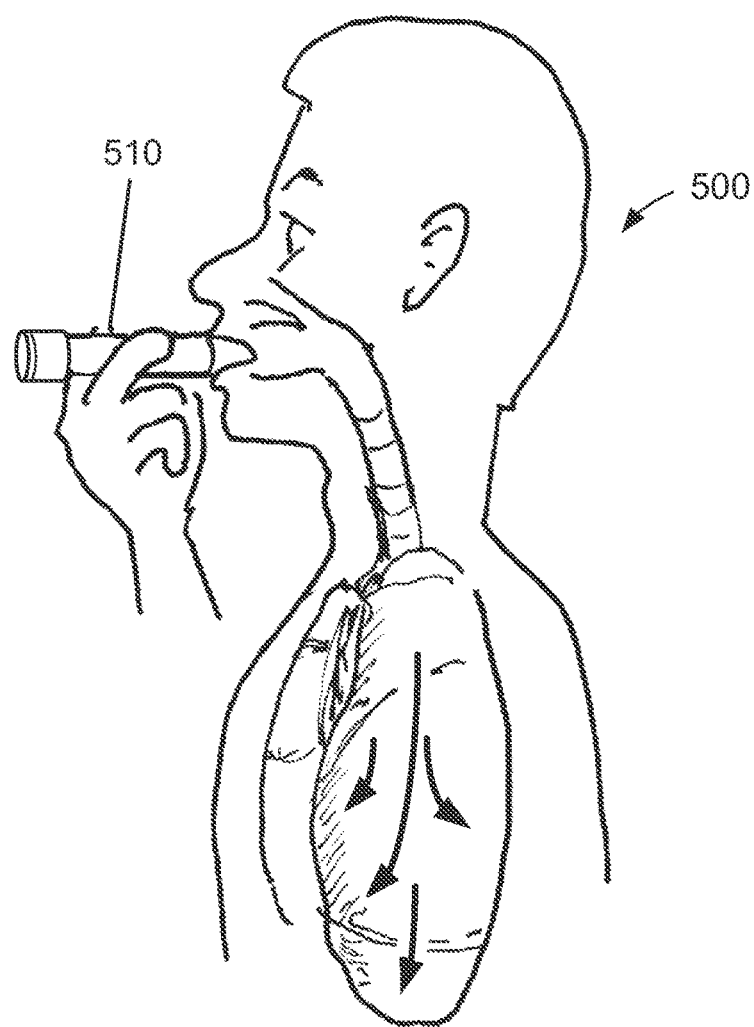
FIG. 5 illustrates a user using an inhaler, according to any of the embodiments described herein.

FIG. 5 illustrates a user 500 using an inhaler 510, according to any of the embodiments described herein. Embodiments described herein enable a device to perform the stated functions in a manner that is specific to characteristics or conditions of a given user (e.g. user's inhalation velocity profile). Furthermore, embodiments described herein enable the inhalant to achieve deep penetration into the respiratory system of the user. For example, the user may be afflicted with a medical condition that causes the user to have shallow breaths. For such persons, the inhalation velocity may be determined and then used to time the release of the inhalant 512 to maximize penetration in the lung, including optionally at the bottom sections of the lung (e.g. the deep lung volume).

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, various embodiments can be adapted for users having particular levels of respiratory compromise as well as for various pediatric applications. Also, various embodiments can be adapted for the dispensing of particular drugs having particular particle sizes and particle size distributions.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for operating an inhaler to deliver a therapeutic agent to a user, the method comprising:
   deriving an inhalation velocity profile for an initial first inhalation, of the user; and
   dispensing the aerosoled form of the therapeutic agent into the lung of the user during the initial first inhalation, wherein dispensing the aerosoled form of the therapeutic agent during the initial first inhalation is based at least in part on the derived inhalation velocity profile; and
   signaling the user when a desired amount of the therapeutic agent has been dispensed.

2. The method of claim 1, wherein deriving the inhalation velocity profile includes determining, from the initial first inhalation, at least one of (i) a duration of maximum inhalation velocity of the derived inhalation velocity profile or (ii) a maximum acceleration of the derived inhalation velocity profile.

3. The method of claim 2, wherein dispensing the aerosoled form of the therapeutic agent is during the initial first inhalation is timed to occur at a time of (i) maximum inhalation velocity, or a (ii) maximum inhalation acceleration.

4. The method of claim 1, wherein dispensing the aerosoled form of the therapeutic agent during an initial first inhalation includes delivering a therapeutically effective amount of the therapeutic agent to a deep lung volume of the user.

5. The method of claim 1, further comprising:
   aerosolizing the therapeutic agent from a non-aerosoled form into an aerosoled form prior to or during the initial first inhalation.

6. The method of claim 5, further comprising controlling the aerosolizing of the therapeutic agent for the initial first inhalation based on the inhalation velocity profile.

7. The method of claim 6, wherein controlling the aerosolizing of the therapeutic agent includes modulating a frequency of a vibrating member that aerosolizes the therapeutic agent using the inhalation velocity profile.

8. The method of claim 1, wherein dispensing the aerosoled form of the therapeutic agent includes generating a driving pressure for assisting in a delivery of the therapeutic agent into the user's lung during the initial first inhalation.

9. The method of claim 8, further comprising:
   modulating the driving pressure based on the derived inhalation velocity profile and responsive to an inhalation velocity of the initial first inhalation.

10. The method of claim 9, wherein modulating the driving pressure includes maintaining a substantially uniform delivery of therapeutic agent over a period of in which the therapeutic agent is dispensed.

11. The method of claim 1, wherein the therapeutic agent comprises insulin, mammalian insulin, human insulin or synthetically derived insulin.

12. The method of claim 1, wherein the therapeutic agent comprises a therapeutic agent for treatment of asthma.

13. The method of claim 1, wherein the therapeutic agent comprises an amino-sulfonyl-benzoate compound, furosemide, bumetanide, torsemide or ethacrynic acid.

14. The method of claim 1, wherein the desired amount is based on the derived inhalation velocity profile and one or more characteristics of the therapeutic agent wherein, the one or more characteristics includes at least one of a particle size, particle weight and absorptiveness of the therapeutic agent.

15. The method of claim 1, wherein signaling the user when the desired amount of the therapeutic agent has been dispensed includes causing the inhaler to generate an audible beep.

16. The method of claim 1, wherein signaling the user when the desired amount of the therapeutic agent has been dispensed includes causing the inhaler to cease generating an audible beep.

* * * * *